US007781404B2

(12) United States Patent
Glass

(10) Patent No.: US 7,781,404 B2

(45) Date of Patent: Aug. 24, 2010

(54) IGF-1 AND IGF-2 CHIMERIC POLYPEPTIDES AND THERAPEUTIC USES THEREOF

(75) Inventor: David J. Glass, Cortlandt Manor, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 12/393,414

(22) Filed: Feb. 26, 2009

(65) Prior Publication Data

US 2009/0175864 A1 Jul. 9, 2009

Related U.S. Application Data

(62) Division of application No. 11/395,706, filed on Mar. 31, 2006, now Pat. No. 7,521,211.

(60) Provisional application No. 60/668,335, filed on Apr. 5, 2005.

(51) Int. Cl.
*A61K 38/30* (2006.01)

(52) U.S. Cl. ........................................................ 514/12

(58) Field of Classification Search ....................... None
See application file for complete search history.

(56) References Cited

U.S. PATENT DOCUMENTS 7,355,018 B2 4/2008 Glass
7,396,918 B2 7/2008 Glass et al.
2003/0072761 A1 4/2003 LeBowitz et al.
2005/0287151 A1 12/2005 Glass
2006/0166328 A1 7/2006 Glass et al.
2007/0087411 A1 4/2007 Sharma et al.

OTHER PUBLICATIONS

Cantley, Lewis C. 2002. The Phosphoinositide 3-Kinase Pathway. Science 296: 1655-1657.

Bodine, Sue C. et al. 2001. Akt/mTOR pathway is a crucial regulator of skeletal muscle hypertrophy and can prevent muscle atropy in vivo. Nature Cell Biology 3: 1014-1019.

Datta, Sandeep Robert et al. 1999. Cellular survival: a play in three Akts. Genes and Development 13: 2905-2927.

Vivanco, Igor and Charles L. Sawyers. 2002. The phosphatidylinositol 3-kinase-akt pathway in human cancer. Nature Reviews 2: 489-501.

*Primary Examiner*—Marianne P Allen
(74) *Attorney, Agent, or Firm*—Valeta Gregg, Esq.; Izumi Yokoyama, Esq.

(57) ABSTRACT

Pharmaceutical compositions containing a chimeric protein comprising an IGF1 and an IGF2 component and optionally (F), a fusion component, and/or a signal sequence, are provided. The chimeric protein exhibits improved activity relative to the native IGF1 or IGF2 polypeptide. Further, therapeutic methods for treating IGF1 insufficiency diseases or conditions using the pharmaceutical compositions of the invention are also provided. The diseases or conditions treatable with the methods include muscle atrophy as a result of, for example, aging, cachexia, rheumatoid arthritis, diabetes, disuse or immobilization of muscle, and the like, as well as dwarfism and myocardial infarction.

8 Claims, No Drawings

IGF-1 AND IGF-2 CHIMERIC POLYPEPTIDES AND THERAPEUTIC USES THEREOF

CROSS-REFERENCE TO RELATED APPLICATIONS

This application is a divisional application of U.S. non-provisional application Ser. No. 11/395,706 filed Mar. 31, 2006, now U.S. Pat. No. 7,521,211, which claims the benefit under 35 USC §119(e) of U.S. provisional application No. 60/668,335 filed Apr. 5, 2005, all of which are herein specifically incorporated by reference in their entireties.

BACKGROUND

1. Field of the Invention

This invention relates to insulin-like growth factor I (IGFI) and insulin-like growth factor 2 (IGF2) chimeric polypeptides, methods of producing such polypeptides, and therapeutic methods for administering such polypeptides.

2. Description of Related Art

The insulin-like growth factors (IGFs) constitute a family of proteins having insulin-like and growth stimulating properties. Human IGFI (also known as somatomedin C) is a 70 aa basic peptide (pl 8.4) having the protein and DNA sequences shown in SEQ ID NOs:1-2, and has a 43% homology with proinsulin (Rinderknecht et al. (1978) J. Biol. Chem. 253: 2769-2776). Human IGF2 is a 67 amino acid basic peptide having the protein and DNA sequences shown in SEQ ID NOs:3-4. Specific binding proteins of high molecular weight having very high binding capacity for IGF1 and IGF2 act as carrier proteins or as modulators of IGF1 functions (Holly et al. (1989) J. Endocrinol. 122:611-618).

IGFI and IGF2 and variants thereof have been used to treat humans suffering from growth hormone deficiencies, tissue wasting, burns, skeletal trauma, infection, cancer, cystic fibrosis, Duchenne muscular dystrophy, Becker dystrophy, autosomal recessive dystrophy, polymyositis, as well as myopathies and AIDS (U.S. Pat. No. 5,622,932). IGF fusion proteins composed of portions of both IGF-1 and IGF-2 have been used as therapeutics for targeting the brain (US 2003/0072761).

BRIEF SUMMARY OF THE INVENTION

In the broadest embodiment, the present invention features compositions comprising IGF2-IGF1 and IGF1-IGF2 chimeric molecules, and methods for treating a subject in need thereof. The IGF2-IGF1 chimeric polypeptides of the invention are more therapeutically active than naturally occurring IGF1 or IGF2 molecules. The chimeric polypeptides of the invention can also be used in a variety of in vitro and in vivo diagnostic and prognostic assays.

In a first aspect, the invention features an IGF2-IGF1 chimeric polypeptide, comprising (a) an IGF2-derived component comprising about amino acid 7 through about amino acid 37 of IGF2 (SEQ ID NO:3), (b) an IGF1-derived component comprising about amino acid 38 to about amino acid 64 of IGF1 (SEQ ID NO:1), and optionally, (c) a fusion component and optionally (d) a signal sequence.

In a second aspect, the invention features an IGF1-IGF2 chimeric polypeptide, comprising (a) an IGF1-derived component comprising about amino acid 4 to amino acid 36 of SEQ ID NO:1, (b) an IGF2 derived component comprising about amino acid 39 to about amino acid 64 of IGF2 (SEQ ID NO:3), and optionally, (c) a fusion component, and optionally (d) a signal sequence.

In a specific embodiment, the invention features an IGF2-IGF1 or IGF1-IGF2 chimeric polypeptide comprising the protein of SEQ ID NO:5, SEQ ID NO:7 or SEQ ID NO:9 or SEQ ID NO:11.

The fusion component (F) includes any component that enhances the functionality of the chimeric polypeptide. Thus, for example, an F may enhance the biological activity of the chimeric polypeptide, aid in its production and/or recovery, or enhance a pharmacological property or the pharmacokinetic profile of the chimeric polypeptide by, for example, enhancing its serum half-life, tissue penetrability, lack of immunogenicity, and/or stability. In a preferred embodiment, the fusion component allows the chimera to evade serum binding proteins which may sequester it into a less biologically active compartment.

In preferred embodiments, F is a multimerizing component selected from the group consisting of (i) an amino acid sequence between 1 to about 500 amino acids in length, optionally comprising at least one cysteine residue, (ii) a leucine zipper, (iii) a helix loop motif, (iv) a coil-coil motif, and (v) an immunoglobulin domain. In some embodiments, the chimeric component comprises an immunoglobulin-derived domain from, for example, human IgG, IgM or IgA. In specific embodiments, the immunoglobulin-derived domain is selected from the group consisting of the Fc domain of IgG, and the heavy chain of IgG. The Fc domain of IgG may be selected from the isotypes IgG1, IgG2, IgG3, and IgG4, as well as any allotype within each isotype group.

In other embodiments, the fusion component (F) comprises a targeting ligand, or derivative or fragment thereof, capable of binding specifically to a pre-selected cell surface protein, and thereby delivering said IGF2-IGF1 or IGF1-IGF2 chimera to a target cell, e.g. a muscle cell. In specific embodiments, the targeting component comprises a MuSK ligand, or a fragment of a MuSK ligand capable of binding the MuSK receptor. In specific embodiments, the MuSK-specific ligand is agrin or a fragment or derivative thereof capable of binding MuSK, or an anti-MuSK antibody or fragment or derivative thereof, including, for example, an scFv. In other specific embodiments, the muscle-targeting ligand of the muscle-targeting chimeric polypeptide comprises three or more muscle cadherin (M-cadherin) extracellular cadherin domains, or derivatives or fragments thereof, capable of binding specifically to a muscle cells or other cells that express homophilic muscle cadherins. In one specific embodiment, the muscle-targeting ligand consists essentially of the first three (3) or four (4) N-terminal extracellular domains of M-cadherin.

In other embodiments, the fusion component (F) of the invention comprises another active compound, which may be any agent that is desirable to deliver to a pre-selected site for therapeutic purposes. In specific embodiments, the active or therapeutic agent comprises a ligand for a second cell surface receptor, and is capable of binding and activating a second receptor. In other embodiments, the active or therapeutic agent comprises an agent capable of blocking the activity of another agent that is active on the target cell. In a specific embodiment, the active or therapeutic agent is selected from the group consisting of IL-15, myotrophin, urocortin, urocortin 11, insulin, the pro domain of myostatin, hGH, proliferin, follistatin, FSTL1, and FLRG, and a biologically active fragment thereof.

The chimeric polypeptide of the invention may further optionally comprise a signal sequence (SS) component. When a SS is part of the polypeptide, any SS known to the art may be used, including synthetic or natural sequences from any source, for example, from a secreted or membrane bound protein. Generally, a signal sequence is placed at the beginning or amino-terminus of a chimeric polypeptide of the invention.

The components of the chimeric polypeptides of the invention may be connected directly to each other or connected via one or more spacer sequences. In one preferred embodiment, the components are fused directly to each other. In another preferred embodiment, the components are connected with a spacer of 1-200 amino acids. Any spacer known to the art may be used to connect the polypeptide components. A spacer sequence may also include a sequence used to enhance expression of the chimeric polypeptide, provide restriction sites, and allow component domains to form optimal tertiary and quaternary structures and/or to enhance the interaction of a component with its receptor. In one embodiment, the chimeric polypeptide of the invention comprises one or more peptide sequences between one or more components which is (are) between 1-25 amino acids.

In a third aspect, the invention features a nucleic acid encoding a chimeric polypeptide of the invention. In specific embodiments, the nucleic acid has a sequence as set forth in SEQ ID NO:6, SEQ ID NO:8 or SEQ ID NO:10 or SEQ ID NO:12.

In a fourth aspect, the invention features a vector comprising a nucleic acid molecule of the invention. In further fifth and sixth aspects, the invention encompasses vectors comprising the nucleic acid molecules of the invention, including expression vectors comprising the nucleic acid molecules operatively linked to an expression control sequence, and host-vector systems for the production of a chimeric polypeptide which comprise the expression vector, in a suitable host cell; host-vector systems wherein the suitable host cell is, without limitation, a bacterial, yeast, insect, or mammalian cell. Examples of suitable cells include *E. coli, B. subtilis*, BHK, COS and CHO cells. Additionally encompassed are chimeric polypeptides of the invention modified by acetylation or pegylation. Methods for acetylating or pegylating a protein are well known in the art.

In a seventh aspect, the invention features a method of producing a chimeric polypeptide of the invention, comprising culturing a host cell transfected with a vector comprising a nucleic acid molecule of the invention, under conditions suitable for expression of the protein from the host cell, and recovering the polypeptide so produced.

In a eighth aspect, the invention features therapeutic methods for the treatment of a disease or condition, comprising administering a therapeutically effective amount of an IGF chimeric protein of the invention to a subject in need thereof, or a subject at risk for development of that disease or condition. When the disease or condition is a muscle condition, such as atrophy, the therapeutic method of the invention comprises administering a therapeutically effective amount of an IGF chimeric protein of the invention to a subject in need thereof, wherein the muscle-related disease or condition is ameliorated or inhibited. The muscle-related condition or disorder treated by the chimeric polypeptides of the invention may arise from a number of sources, including, for example, denervation; degenerative, metabolic or inflammatory neuropathy; infantile and juvenile spinal muscular atrophies; autoimmune motor neuropathy; from chronic disease, including cachexia resulting from cancer, AIDS, fasting or rhabdomyolysis; and from muscular dystrophy syndromes such as Duchenne. The therapeutic methods of the invention are useful to treat any condition which results from an IGF deficiency or which may be improved by increased IGF levels, including dwarfism and heart disease, for example, improved heart tissue survival following myocardial infarction.

Accordingly, in an ninth aspect, the invention features pharmaceutical compositions comprising a chimeric protein of the invention with a pharmaceutically acceptable carrier. Such pharmaceutical compositions may comprise a chimeric protein or a nucleic acid that encodes it, together with a pharmaceutically acceptable carrier.

Other objects and advantages will become apparent from a review of the ensuing detailed description.

DETAILED DESCRIPTION

As used in this specification and the appended claims, the singular forms “a”, “an”, and “the” include plural references unless the context clearly dictates otherwise. Thus for example, references to “a method” include one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, preferred methods and materials are now described. All publications mentioned herein are incorporated herein by reference.

General Description

The invention encompasses chimeric polypeptides and nucleic acids that encode them which comprise an IGF1 and an IGF2 derived component and optionally a fusion component (F), which may comprise a multimerizing component, a targeting component, and/or one or more additional active or therapeutic agent(s).

Definitions

“Biologically active” fragments or derivatives of a component of the chimeric polypeptides of the invention encompass any naturally occurring or synthetic molecule, mutant, or derivative thereof capable of achieving the desired effect. For example, described herein are chimeras containing components derived from IGF1 and IGF2, which have improved properties of activity. The invention includes the use of a mutant or derivative of the IGF1 and IGF2-derived molecules described herein which are capable of binding the IGF1 receptor. A “biologically active” fragment or derivative of any targeting component includes any portion or mutant thereof capable of binding a target cell. Thus, for example, when the targeting ligand is agrin, a biologically active fragment or derivative is any portion or mutant of agrin capable of binding the MuSK receptor.

The terms “treatment”, “treating”, and the like include obtaining a desired pharmacologic and/or physiologic effect. The effect may be prophylactic in terms of completely or partially preventing a disease, condition, or symptoms thereof, and/or may be therapeutic in terms of a partial or complete cure for a disease or condition and/or adverse effect attributable to the disease or condition. “Treatment” as used herein covers any treatment of a disease or condition of a mammal, particularly a human, and includes: (a) preventing the disease or condition from occurring in a subject which may be predisposed to the disease or condition but has not yet been diagnosed as having it; (b) inhibiting the disease or condition, i.e., arresting its development; or (c) relieving the disease or condition, i.e., causing regression of the disease or condition. The population of subjects treated by the method of the disease includes subjects suffering from the condition or disease, as well as subjects at risk for developing the condition or disease.

By the term "therapeutically effective dose" includes a dose that produces the desired effect for which it is administered. The exact dose will depend on the purpose of the treatment, and will be ascertainable by one skilled in the art using known techniques (see, for example, Lloyd (1999) The Art, Science and Technology of Pharmaceutical Compounding).

As used herein, a "condition or disease" generally includes a condition of a mammalian host, particularly a human host, which is undesirable and/or injurious to the host. Thus, treating a muscle-related condition with a chimeric polypeptide which specifically targets skeletal muscle will encompass the treatment of a mammal, in particular, a human, who has symptoms reflective of decreased target muscle receptor activation, or who is expected to have such decreased levels in response to a disease, condition or treatment regimen. Treating a muscle-related condition or disease includes treating a human subject wherein enhancing the activation of a target muscle receptor with the muscle specific chimeric polypeptide of the invention results in amelioration of an undesirable symptom resulting from the muscle-related condition or disease. As used herein, a "muscle-related condition" also includes a condition in which it is desirable to alter, either transiently or long-term, activation of a particular target muscle receptor.

IGF2-IGF1 and IGF1-IGF2 Chimeras

The first component of the IGF2-IGF1 chimeric polypeptides of the invention is derived from IGF2. This component comprises about amino acid 7 to about amino acid 37 of human IGF2 (SEQ ID NO:3). This component may also include amino acids 1-6 of the IGF2 protein, preferably with substitution of Glu6 with a different amino acid. The second component of the IGF2-IGF1 chimeras of the invention comprises about amino acid 38 to about amino acid 64 of IGF1 (SEQ ID NO:1). This component may include the amino acids 65-70 of the C-terminus of IGF1. In preferred embodiments, when a fusion component (F) is used in conjunction with the chimeric polypeptide, these six amino acids are either deleted (Δ65-70) or have a modification selected from the group consisting of deletion of 3-5 amino acids, e.g., 68-70 (Δ68-70, Δ67-70, or Δ66-70), deletion of Lys68 (Δ68), substitution of amino acid 68 with another amino acid, deletion of Lys65 (Δ65), and substitution of amino acid 65 with another amino acid. In specific embodiments the chimeric protein comprises the sequence set forth in SEQ ID NO:5 or SEQ ID NO:7.

The first component of the IGF1-IGF2 chimeric polypeptides of the invention is derived from IGF1 and comprises about amino acid 4 to amino acid 36 of SEQ ID NO:1. This component may also include amino acids 1-3 of the IGF1 protein, preferably with substitution of Glu3 with a different amino acid. The second component of the IGF1-IGF2 chimeric polypeptides of the invention comprises about amino acid 39 to about amino acid 64 of IGF2. This component may also include amino acids 65-67 of the C-terminus of IGF2. In preferred embodiments, when a fusion component (F) is used in conjunction with the chimeric polypeptide, these three amino acids are either deleted (Δ65-67) or modified with a deletion of Lys65 (Δ65), or substitution of amino acid Lys65 with another amino acid. In a specific embodiment, the chimeric polypeptide has a sequence as set forth in SEQ ID NO:9 or SEQ ID NO:11.

In the above embodiments of the chimeras wherein a fusion component is used, the C-terminal modifications have been found to prevent the cleavage of the fusion component from the IGF2-IGF1 or IGF1-IGF2 variant, thus enhancing their stability and half-life.

Fusion Component

In some embodiments, the fusion component of the chimeric polypeptides of the invention is a targeting ligand. A targeting ligand is a molecule, e.g., a protein or fragment thereof that specifically binds with high affinity to a target on a pre-selected cell, for example, a surface protein such as a receptor that is present to a greater degree on the pre-selected cell target than on any other body tissue. For example, as described in U.S. Pat. Nos. 5,814,478 and 6,413,740, the MuSK receptor is highly specific to muscle. Accordingly, the cognate ligand agrin, as well as MuSK binding portions thereof, is an example of a targeting ligand useful as a chimeric component in the chimeric polypeptides of the present invention. Another example of a targeting ligand is a group of cadherin domains from a human cadherin. Accordingly, human cadherin domains from, for example, human muscle cadherin, may be used in the targeting chimeric polypeptides of the invention to target muscle cells. The targeting ligand component of the chimeric polypeptide of the invention may include a naturally occurring or engineered ligand, or a fragment thereof, capable of binding the pre-selected target cell.

In another embodiment of the invention, the targeting ligand component of the chimeric polypeptides of the invention consists of at least three, four or five muscle cadherin (M-cadherin) domains, or derivatives or fragments thereof, capable of binding specifically to target cells that express homophilic cadherins (Shimoyama et al. (1998) J. Biol. Chem. 273(16): 10011-10018; Shibata et al. (1997) J. Biol. Chem. 272(8):5236-5270). In preferred embodiments, a chimeric polypeptide of the invention comprises at least three cadherin domains from the extracellular domain of human M-cadherin (or biologically active fragments or derivatives thereof that are capable of binding homophilic M-cadherin), fused to the IGF chimera.

Further examples of targeting ligands also include, but are not limited to, antibodies and portions thereof that bind a pre-selected cell surface protein with high affinity. By "high affinity" is meant an equilibrium dissociation constant of at least $10^{-7}$ molar, as determined by assay methods known in the art, for example, BIAcore analysis. In one embodiment, the targeting ligand component of the targeting chimeric polypeptides of the invention may also comprise one or more immunoglobulin binding domains isolated from antibodies generated against a selected tissue-specific surface protein or target tissue-specific receptor. The term "immunoglobulin or antibody" as used herein includes a mammalian, including human, polypeptide comprising a framework region from an immunoglobulin gene or fragments thereof that specifically binds and recognizes an antigen, which, in the case of the present invention, is a tissue-specific surface protein, a target tissue-specific receptor, or portion thereof. If the intended targeting chimeric polypeptide will be used as a mammalian therapeutic, immunoglobulin binding regions should be derived from the corresponding mammalian immunoglobulins. If the targeting chimeric polypeptide is intended for non-therapeutic use, such as for diagnostics and ELISAs, the immunoglobulin binding regions may be derived from either human or non-human mammals, such as mice. The human immunoglobulin genes or gene fragments include the kappa, lambda, alpha, gamma, delta, epsilon, and mu constant regions, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD, and IgE, respectively. Within each IgG class, there are different isotypes (e.g., $IgG_1$, $IgG_2$, etc.). Typically, the antigen-binding region of an antibody will be the most critical in determining specificity and affinity of binding.

Active or Therapeutic Agent

In some embodiments, the fusion component (F) of the polypeptides of the invention comprises a second active or therapeutic agent or mutant or derivative thereof, i.e., a molecule capable of having a desired effect when delivered to the pre-selected target site, e.g., cell or tissue. Active or therapeutic agents, include, but are not limited to, small molecules, hormones, growth factors, therapeutic biologics, activating antibodies and portions thereof, and blocking antibodies and portions thereof, that are capable of having a desirable effect upon delivery to a target cell or tissue.

In particular embodiments wherein the chimeric polypeptide is directed at muscle cells or tissue, the chimeric polypeptide comprises a second active or therapeutic agent that is active on muscle cells. Such agents include, but are not limited to, insulin, IL-15, myotrophin, urocortin, urocortin II, human myostatin propeptide, hGH, proliferin, follistatin, FSTL1, and FLRG, or mutants, derivatives, or fragments thereof having biological activity. In addition, the active or therapeutic agent may comprise a blocking antibody or biologically active derivative thereof, which blocks, for example, myostatin, activin receptor, BMP receptor 1, TNF receptor, IL-1 receptor, ALK3 receptor and ALK4 receptor. Alternatively, the active or therapeutic agent may comprise an activating antibody that activates, for example, the IFG1 receptor, B2adrenergic receptor or the IL-15 receptor complex.

Multimerizing Component

In specific embodiments, the fusion component (F) of the chimeric polypeptides of the invention comprises a multimerizing component. A multimerizing component includes any natural or synthetic sequence capable of interacting with another multimerizing component to form a higher order structure, e.g., a dimer, a trimer, etc. The multimerizing component may be selected from the group consisting of an amino acid sequence between 1 to about 500 amino acids in length, a leucine zipper, a helix loop motif, and a coil-coil motif. When the multimerizing component comprises an amino acid sequence between 1 to about 500 amino acids in length, the sequence may contain one or more cysteine residues capable of forming a disulfide bond with a corresponding cysteine residue on another chimeric polypeptide comprising a multimerizing component with one or more cysteine residues. In some embodiments, the multimerizing component comprises an immunoglobulin-derived domain from, for example, human IgG, IgM or IgA, or comparable immunoglobulin domains from other animals, including, but not limited to, mice. In specific embodiments, the immunoglobulin-derived domain may be selected from the group consisting of the constant region of IgG, the Fc domain of IgG, an Fc-protein, and the heavy chain of IgG. The Fc domain of IgG may be selected from the isotypes IgG1, IgG2, IgG3, and IgG4, as well as any allotype within each isotype group.

Component Spacers

The components of the chimeric polypeptides of the invention may be connected directly to each other or may be connected via spacers. The term "spacer" or "linker" means one or more molecules, e.g., nucleic acids or amino acids, or non-peptide moieties, such as polyethylene glycol, which may be inserted between one or more component domains. For example, spacer sequences may be used to provide a restriction site between components for ease of manipulation. A spacer may also be provided to enhance expression of the chimeric polypeptide from a host cell, to decrease steric hindrance such that the component may assume its optimal tertiary or quaternary structure and/or interact appropriately with its target molecule. For spacers and methods of identifying desirable spacers, see, for example, George et al. (2003) Protein Engineering 15:871-879, herein specifically incorporated by reference.

A spacer sequence may include one or more amino acids naturally connected to a receptor component, or may be an added sequence used to enhance expression of the chimeric protein, provide specifically desired sites of interest, allow component domains to form optimal tertiary structures and/or to enhance the interaction of a component with its target molecule. In some embodiments, the spacer comprises one or more peptide sequences between one or more components which is (are) between 1-100 amino acids, preferably 1-25. In a specific embodiment, the spacer is a three amino acid sequence; more specifically, the three amino acid sequence of Gly Pro Gly.

Nucleic Acid Construction and Expression

Individual components of the chimeric polypeptides of the invention may be produced from nucleic acids molecules using molecular biological methods known to the art. The nucleic acid of SEQ ID NO:6, SEQ ID NO:8 or SEQ ID NO:10 or SEQ ID NO:12 with the appropriate deletions or mutations may be used to prepare the IGF chimeras described herein. Such nucleic acid molecules are inserted into a vector that is able to express the chimeric polypeptides when introduced into an appropriate host cell. Appropriate host cells include, but are not limited to, bacterial, yeast, insect, and mammalian cells. Any of the methods known to one skilled in the art for the insertion of DNA fragments into a vector may be used to construct expression vectors encoding the chimeric polypeptides of the invention under control of transcriptional/translational control signals. These methods may include in vitro recombinant DNA and synthetic techniques and in vivo recombinations (See Sambrook et al. *Molecular Cloning, A Laboratory Manual*, Cold Spring Harbor Laboratory; Current Protocols in Molecular Biology, Eds. Ausubel, et al., Greene Publ. Assoc., Wiley-Interscience, NY).

Expression of the nucleic acid molecules of the invention may be regulated by a second nucleic acid sequence so that the molecule is expressed in a host transformed with the recombinant DNA molecule. For example, expression of the nucleic acid molecules of the invention may be controlled by any promoter/enhancer element known in the art. Promoters which may be used to control expression of the chimeric polypeptide molecules include, but are not limited to, the long terminal repeat as described in Squinto et al. (1991) Cell 65:1-20; the SV40 early promoter region, the CMV promoter, the M-MuLV 5' terminal repeat the promoter contained in the 3' long terminal repeat of Rous sarcoma virus, the herpes thymidine kinase promoter, the regulatory sequences of the metallothionine gene; prokaryotic expression vectors such as the β-lactamase promoter, or the tac promoter (see also "Useful proteins from recombinant bacteria" in Scientific American (1980) 242:74-94); promoter elements from yeast or fungi such as the Gal 4 promoter, the ADH (alcohol dehydrogenase) promoter, PGK (phosphoglycerol kinase) promoter, alkaline phosphatase promoter, and tissue-specific transcriptional control regions derived from elastase I gene, insulin gene, immunoglobulin gene, mouse mammary tumor virus, albumin gene, α-fetoprotein gene, α1-antitrypsin gene, β-globin gene, myelin basic protein gene, myosin light chain-2 gene, and gonadotropic releasing hormone gene.

The nucleic acid constructs of the invention are inserted into an expression vector or viral vector by methods known to the art. Also provided is a host-vector system for the production of a tissue-specific chimeric polypeptide of the invention, which comprises the expression vector of the invention, which has been introduced into a host cell suitable for expression of the chimeric polypeptide. The suitable host cell may be a bacterial cell such as *E. coli*, a yeast cell, such as *Pichia pastoris*, an insect cell, such as *Spodoptera frugiperda*, or a mammalian cell, such as a COS, CHO, 293, BHK or NS0 cell.

The invention further encompasses methods for producing the chimeric polypeptides of the invention by growing cells transformed with an expression vector under conditions permitting production of the tissue-specific chimeric polypeptides and recovery of the chimeric polypeptides so produced. Cells may also be transduced with a recombinant virus comprising a nucleic acid construct of the invention.

The chimeric polypeptides may be purified by any technique that allows for the subsequent formation of a stable polypeptide. For example, and not by way of limitation, the chimeric polypeptides may be recovered from cells either as soluble polypeptides or as inclusion bodies, from which they may be extracted quantitatively by 8M guanidinium hydrochloride and dialysis. In order to further purify the chimeric polypeptides, conventional ion exchange chromatography, hydrophobic interaction chromatography, reverse phase chromatography or gel filtration may be used. The chimeric polypeptides may also be recovered from conditioned media following secretion from eukaryotic or prokaryotic cells.

Therapeutic Methods

The invention herein further provides for the development of IGF chimeric polypeptides described herein as a therapeutic for the treatment of patients suffering from disorders, for example, muscle atrophy, which may be ameliorated by providing IGF1 or IGF2. For example, a decrease in muscle mass, or atrophy, is associated with various physiological and pathological states. Muscle atrophy can result from aging, AIDS-induced cachexia, anemia, burns, cancer-induced cachexia, casting, congestive heart failure, settings wherein inflammatory cytokines such as IL-1 or TNF-α are in excess, denervation, diabetes, disuse (such as in prolonged bed rest), growth hormone deficiency, IGF1-deficiency, immobilization, inflammation, such as in chronic inflammatory conditions such as rheumatoid arthritis, mechanic ventilation (resulting in atrophy of the diaphragm), renal failure, sarcopenia, and sepsis-induced cachexia. Muscle atrophy can result from denervation due to nerve trauma; degenerative, metabolic or inflammatory neuropathy, e.g., Guillian-Barré syndrome; peripheral neuropathy; or nerve damage caused by environmental toxins or drugs. Muscle atrophy may also result from denervation due to a motor neuropathy including, for example, adult motor neuron disease, such as Amyotrophic Lateral Sclerosis (ALS or Lou Gehrig's disease); infantile and juvenile spinal muscular atrophies; and autoimmune motor neuropathy with multifocal conductor block. Muscle atrophy may also result from chronic disease resulting from, for example, paralysis due to stroke or spinal cord injury; skeletal immobilization due to trauma, such as, for example, fracture, ligament or tendon injury, sprain or dislocation; or prolonged bed rest. Metabolic stress or nutritional insufficiency, which may also result in muscle atrophy, include the cachexia of cancer and other chronic illnesses including AIDS, fasting or rhabdomyolysis, and endocrine disorders such as disorders of the thyroid gland and diabetes. Muscle atrophy may also be due to muscular dystrophy syndromes such as Duchenne, Becker, myotonic, fascioscapulohumeral, Emery-Dreifuss, oculopharyngeal, scapulohumeral, limb girdle, and congenital types, as well as the dystrophy known as Hereditary Distal Myopathy. Muscle atrophy may also be due to a congenital myopathy, such as benign congenital hypotonia, central core disease, nemalene myopathy, and myotubular (centronuclear) myopathy. Muscle atrophy also occurs during the aging process. Muscle atrophy in various pathological states is associated with enhanced proteolysis and decreased production of muscle proteins.

The IGF chimeric polypeptides of the invention are also useful in diseases associated with an IGF deficiency, such as dwarfism. Still further, IGFs have been shown to improve the survival of cardiac muscle cells after an event such as a myocardial infarction, thus the chimeric polypeptides of the invention are useful in a subject who has experienced such an event. The chimeric polypeptides of the invention are also useful in the treatment for glucocorticoid induced side effects, such as osteoporosis, muscle atrophy, and renal failure.

The ability of the IGF chimeric polypeptides of the invention to evade the large number of IGF-binding proteins present in a mammal makes them therapeutically useful for efficiently treating conditions which may benefit from an increased IGF level, such as recovery from atrophy-promoting conditions, situations in which skeletal muscle mass decreases, or situations in which muscle hypertrophy is desirable, such as during recovery from immobilization, aging, cancer, etc.

Because IGF receptors are expressed broadly, IGF chimeric molecules of the invention wherein the fusion component is a multimerizing component such as Fc or another active component could further be used in settings other than muscle. For example, IGF1 and IGF2 have been shown to be bone growth factors, and therefore an IGF chimera fused to growth hormone could be useful in the treatment of osteoporosis or other bone loss or weakness, including age related weakness, frailty or sarcopenia. The non-targeting molecules may also be useful in settings of more general body mass wasting—such as cachexia. Cachexia is a condition causing body mass loss, including, but not limited to, muscle mass. Settings of cachexia include cancer-induced cachexia, AIDS-induced cachexia, sepsis-induced cachexia, renal failure-induced cachexia, and congestive heart failure. Also, there is growth retardation in many settings, including thalassaemia, which causes short stature. Short stature in general would be a setting for an IGF chimeric protein that is not targeted directly to muscle—such as the IGF chimera-Fc or the IGF chimera-GH embodiments. An additional use for IGF chimeras is to complement or substitute for insulin. In settings of insulin-insensitive diabetes, IGF chimeric proteins of the invention may be used. Such variants may further be used simply as a substitute for insulin in settings of hyperglycemia. Further additional uses for the IGF chimeras described herein include use in the weaning of individuals from ventilators and for the treatment of conditions such as anemia wherein the proliferation of blood cells is desired.

Methods of Administration

Methods known in the art for the therapeutic delivery of agents such as proteins or nucleic acids can be used for the therapeutic delivery of an IGF chimeric polypeptide or a nucleic acid encoding a IGF chimeric polypeptide of the invention, e.g., cellular transfection, gene therapy, direct administration with a delivery vehicle or pharmaceutically acceptable carrier, indirect delivery by providing recombinant cells comprising a nucleic acid encoding an IGF chimeric polypeptide of the invention.

Various delivery systems are known and can be used to administer the chimeric polypeptide of the invention, e.g., encapsulation in liposomes, microparticles, microcapsules, recombinant cells capable of expressing the compound, receptor-mediated endocytosis (see, e.g., Wu and Wu, 1987, J. Biol. Chem. 262:4429-4432), construction of a nucleic acid as part of a retroviral or other vector, etc. Methods of introduction can be enteral or parenteral and include but are not limited to intradermal, intramuscular, intraperitoneal, intravenous, subcutaneous, pulmonary, intranasal, intraocular, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved, for example, and not by way of limitation, by local infusion during surgery, topical application, e.g., by injection, by means of a catheter, or by means of an implant, said implant being of a porous, non-porous, or gelatinous material, including membranes, such as sialastic membranes, fibers, or commercial skin substitutes.

In another embodiment, the active agent can be delivered in a vesicle, in particular a liposome (see Langer (1990) Science 249:1527-1533). In yet another embodiment, the active agent can be delivered in a controlled release system. In one embodiment, a pump may be used (see Langer (1990) supra). In another embodiment, polymeric materials can be used (see Howard et al. (1989) J. Neurosurg. 71:105). In another embodiment where the active agent of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see, for example, U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., 1991, Proc. Natl. Acad. Sci. USA 88:1864-1868), etc. Alternatively, a nucleic acid can be introduced intracellularly and incorporated within host cell DNA for expression by homologous recombination.

Combination Therapies

In numerous embodiments, a chimeric polypeptide of the present invention may be administered in combination with one or more additional compounds or therapies. For example, multiple chimeric polypeptides can be co-administered in conjunction with one or more therapeutic compounds. The combination therapy may encompass simultaneous or alternating administration. In addition, the combination may encompass acute or chronic administration.

Pharmaceutical Compositions

The present invention also provides pharmaceutical compositions comprising a chimeric protein of the invention and a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin.

In a preferred embodiment, the composition is formulated in accordance with routine procedures as a pharmaceutical composition adapted for intravenous administration to human beings. The composition may also include a solubilizing agent and a local anesthetic such as lidocaine to ease pain at the site of the injection. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The active agents of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of chimeric polypeptide of the invention which will be effective in the treatment of a condition or disease can be determined by standard clinical techniques based on the present description. In addition, in vitro assays may optionally be employed to help identify optimal dosage ranges. The precise dose to be employed in the formulation will also depend on the route of administration, and the seriousness of the condition, and can be determined by a person of ordinary skill in the art. However, suitable dosage ranges for intravenous administration are generally about 20-5000 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

Specific Embodiments

Example 1 illustrates specific embodiments of the chimeric polypeptides of the invention, wherein IGF2-IGF1 and IGF1-IGF2 are prepared and tested.

EXAMPLES

The following examples are put forth so as to provide those of ordinary skill in the art with a description of how to make and use methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

IGF2-IGF1 Chimeras

An IGF2-IGF1 chimeric polypeptide and an IGF1-IGF2 chimeric polypeptide having the sequence as set forth in SEQ ID NO:7 and SEQ ID NO:11 respectively were constructed. These chimeras comprise a signal sequence, an N-terminal portion derived from IGF2 or IGF1 (with deletion of 6 or 3 N-terminal amino acids, respectively) and a C-terminal portion derived from IGF1 or IGF2 (with deletion of 6 and 3 C-terminal amino acids, respectively), as well as a fusion component (F) which is human Fc.

Equimolar amounts of IGF1-Fc, IGF2-Fc, and the IGF2/IGF1-Fc and IGF1/IGF2 chimeras were used to stimulate C2C12 myotube cultures for 15 minutes. Protein lysates were then prepared, and run on Western blots. An antibody specific for the phosphorylated form of Akt demonstrated that the IGF2/IGF1-Fc (SEQ ID NO:7) and the IGF1/IGF2-Fc molecule (SEQ ID NO:11) stimulated Akt equal or higher levels than IGF1-Fc.

What is claimed is:

1. A pharmaceutical composition comprising a chimeric IGF polypeptide and a pharmaceutically acceptable carrier, wherein the chimeric IGF polypeptide comprises in an N-terminus to a C-terminus direction: (a) an IGF2-derived component comprising amino acid 7 through amino acid 37 of IGF2 (SEQ ID NO:3) and an IGF-1-derived component comprising amino acid 38 to amino acid 64 of IGF1 (SEQ ID NO:1), or (b) an IGF1-derived component comprising amino acid 4 to amino acid 36 of SEQ ID NO:1 and an IGF2-derived component comprising amino acid 39 to amino acid 64 of IGF2, and optionally (c) a fusion component (F) at the C-terminus, and/or (d) a signal sequence at the N-terminus, wherein F is selected from the group consisting of a human IgG constant region, Fc domain, and heavy chain.

2. The pharmaceutical composition of claim 1, wherein said chimeric IGF polypeptide comprises an amino acid sequence selected from the group consisting of SEQ ID NO:5, SEQ ID NO:7, SEQ ID NO:9 and SEQ ID NO:11.

3. A method for treating a disease or condition which is accompanied by a decrease in muscle mass, comprising administering a therapeutically effective amount of the pharmaceutical composition of claim 2 to a subject in need thereof, thereby ameliorating or improving the decrease in muscle mass.

4. The method of claim 3, wherein the disease or condition is muscle atrophy, or muscular dystrophy.

5. The method of claim 4, wherein muscle atrophy is a result of aging, AIDS-induced cachexia, burns, cancer-induced cachexia, casting, congestive heart failure, rheumatoid arthritis, denervation, diabetes, growth hormone deficiency, IGF1-deficiency, disuse, immobilization, mechanic ventilation, renal failure, sarcopenia, or sepsis-induced cachexia.

6. A method for treating a disease or condition which is accompanied by a decrease in muscle mass, comprising administering a therapeutically effective amount of the pharmaceutical composition of claim 1 to a subject in need thereof, thereby ameliorating or improving the decrease in muscle mass.

7. The method of claim 6, wherein the disease or condition is muscle atrophy, or muscular dystrophy.

8. The method of claim 7, wherein muscle atrophy is a result of aging, AIDS-induced cachexia, burns, cancer-induced cachexia, casting, congestive heart failure, rheumatoid arthritis, denervation, diabetes, growth hormone deficiency, IGF1-deficiency, disuse, immobilization, mechanic ventilation, renal failure, sarcopenia, or sepsis-induced cachexia.

* * * * *

SEQUENCE LISTING

```
<160> NUMBER OF SEQ ID NOS: 12

<210> SEQ ID NO 1
<211> LENGTH: 70
<212> TYPE: PRT
<213> ORGANISM: Homo Sapien

<400> SEQUENCE: 1

Gly Pro Glu Thr Leu Cys Gly Ala Glu Leu Val Asp Ala Leu Gln Phe
 1              5                   10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
        35                  40                  45

Phe Arg Ser Cys Asp Leu Arg Arg Leu Glu Met Tyr Cys Ala Pro Leu
    50                  55                  60

Lys Pro Ala Lys Ser Ala
65                  70


<210> SEQ ID NO 2
<211> LENGTH: 210
<212> TYPE: DNA
<213> ORGANISM: Homo Sapien

<400> SEQUENCE: 2

ggaccggaga cgctctgcgg ggctgagctg gtggatgctc ttcagttcgt gtgtggagac      60

aggggctttt atttcaacaa gcccacaggg tatggctcca gcagtcggag ggcgcctcag     120

acaggtatcg tggatgagtg ctgcttccgg agctgtgatc taaggaggct ggagatgtat     180

tgcgcacccc tcaagcctgc caagtcagct                                      210


<210> SEQ ID NO 3
<211> LENGTH: 67
<212> TYPE: PRT
<213> ORGANISM: Homo Sapien

<400> SEQUENCE: 3

Ala Tyr Arg Pro Ser Glu Thr Leu Cys Gly Gly Glu Leu Val Asp Thr
 1              5                   10                  15

Leu Gln Phe Val Cys Gly Asp Arg Gly Phe Tyr Phe Ser Arg Pro Ala
            20                  25                  30

Ser Arg Val Ser Arg Arg Ser Arg Gly Ile Val Glu Glu Cys Cys Phe
        35                  40                  45

Arg Ser Cys Asp Leu Ala Leu Leu Glu Thr Tyr Cys Ala Thr Pro Ala
    50                  55                  60

Lys Ser Glu
65
```

-continued

```
<210> SEQ ID NO 4
<211> LENGTH: 201
<212> TYPE: DNA
<213> ORGANISM: Homo Sapien

<400> SEQUENCE: 4

gcttaccgcc ccagtgagac cctgtgcggc ggggagctgg tggacaccct ccagttcgtc      60

tgtggggacc gcggcttcta cttcagcagg cccgcaagcc gtgtgagccg tcgcagccgt     120

ggcatcgttg aggagtgctg tttccgcagc tgtgacctgg ccctcctgga gacgtactgt     180

gctacccccg ccaagtccga g                                                201


<210> SEQ ID NO 5
<211> LENGTH: 58
<212> TYPE: PRT
<213> ORGANISM: Artificial Sequence
<220> FEATURE:
<223> OTHER INFORMATION: Synthetic

<400> SEQUENCE: 5

Thr Leu Cys Gly Gly Glu Leu Val Asp Thr Leu Gln Phe Val Cys Gly
 1               5                  10                  15

Asp Arg Gly Phe Tyr Phe Ser Arg Pro Ala Ser Arg Val Ser Arg Ala
            20                  25                  30

Pro Gln Thr Gly Ile Val Asp Glu Cys Cys Phe Arg Ser Cys Asp Leu
        35                  40                  45

Arg Arg Leu Glu Met Tyr Cys Ala Pro Leu
    50                  55


<210> SEQ ID NO 6
<211> LENGTH: 174
<212> TYPE: DNA
<213> ORGANISM: Artificial Sequence
<220> FEATURE:
<223> OTHER INFORMATION: Synthetic

<400> SEQUENCE: 6

accctgtgcg gcggggagct ggtggacacc ctccagttcg tctgtgggga ccgcggcttc      60

tacttcagca ggcccgcaag ccgtgtgagc cgtgcgcctc agacaggcat cgtggatgag     120

tgctgcttcc ggagctgtga tctaaggagg ctggagatgt attgcgcacc cctc           174


<210> SEQ ID NO 7
<211> LENGTH: 309
<212> TYPE: PRT
<213> ORGANISM: Homo sapien

<400> SEQUENCE: 7

Met Gly Ile Pro Met Gly Lys Ser Met Leu Val Leu Leu Thr Phe Leu
 1               5                  10                  15

Ala Phe Ala Ser Cys Cys Ile Ala Thr Leu Cys Gly Gly Glu Leu Val
            20                  25                  30

Asp Thr Leu Gln Phe Val Cys Gly Asp Arg Gly Phe Tyr Phe Ser Arg
        35                  40                  45

Pro Ala Ser Arg Val Ser Arg Ala Pro Gln Thr Gly Ile Val Asp Glu
    50                  55                  60

Cys Cys Phe Arg Ser Cys Asp Leu Arg Arg Leu Glu Met Tyr Cys Ala
65                  70                  75                  80

Pro Leu Asp Lys Thr His Thr Cys Pro Pro Cys Pro Ala Pro Glu Leu
```

-continued

```
                85                  90                  95

Leu Gly Gly Pro Ser Val Phe Leu Phe Pro Pro Lys Pro Lys Asp Thr
            100                 105                 110

Leu Met Ile Ser Arg Thr Pro Glu Val Thr Cys Val Val Val Asp Val
        115                 120                 125

Ser His Glu Asp Pro Glu Val Lys Phe Asn Trp Tyr Val Asp Gly Val
    130                 135                 140

Glu Val His Asn Ala Lys Thr Lys Pro Arg Glu Glu Gln Tyr Asn Ser
145                 150                 155                 160

Thr Tyr Arg Val Val Ser Val Leu Thr Val Leu His Gln Asp Trp Leu
                165                 170                 175

Asn Gly Lys Glu Tyr Lys Cys Lys Val Ser Asn Lys Ala Leu Pro Ala
            180                 185                 190

Pro Ile Glu Lys Thr Ile Ser Lys Ala Lys Gly Gln Pro Arg Glu Pro
        195                 200                 205

Gln Val Tyr Thr Leu Pro Pro Ser Arg Asp Glu Leu Thr Lys Asn Gln
    210                 215                 220

Val Ser Leu Thr Cys Leu Val Lys Gly Phe Tyr Pro Ser Asp Ile Ala
225                 230                 235                 240

Val Glu Trp Glu Ser Asn Gly Gln Pro Glu Asn Asn Tyr Lys Thr Thr
                245                 250                 255

Pro Pro Val Leu Asp Ser Asp Gly Ser Phe Phe Leu Tyr Ser Lys Leu
            260                 265                 270

Thr Val Asp Lys Ser Arg Trp Gln Gln Gly Asn Val Phe Ser Cys Ser
        275                 280                 285

Val Met His Glu Ala Leu His Asn His Tyr Thr Gln Lys Ser Leu Ser
    290                 295                 300

Leu Ser Pro Gly Lys
305
```

<210> SEQ ID NO 8
<211> LENGTH: 927
<212> TYPE: DNA
<213> ORGANISM: Homo sapien

<400> SEQUENCE: 8

```
atgggaatcc caatggggaa gtcgatgctg gtgcttctca ccttcttggc cttcgcctcg     60

tgctgcattg ctaccctgtg cggcggggag ctggtggaca ccctccagtt cgtctgtggg    120

gaccgcggct tctacttcag caggcccgca agccgtgtga gccgtgcgcc tcagacaggc    180

atcgtggatg agtgctgctt ccggagctgt gatctaagga ggctggagat gtattgcgca    240

cccctcgaca aaactcacac atgcccaccg tgcccagcac ctgaactcct ggggggaccg    300

tcagtcttcc tcttcccccc aaaacccaag gacaccctca tgatctcccg gacccctgag    360

gtcacatgcg tggtggtgga cgtgagccac gaagaccctg aggtcaagtt caactggtac    420

gtggacggcg tggaggtgca taatgccaag acaaagccgc gggaggagca gtacaacagc    480

acgtaccgtg tggtcagcgt cctcaccgtc ctgcaccagg actggctgaa tggcaaggag    540

tacaagtgca aggtctccaa caaagccctc ccagccccca tcgagaaaac catctccaaa    600

gccaaagggc agccccgaga accacaggtg tacaccctgc ccccatcccg ggatgagctg    660

accaagaacc aggtcagcct gacctgcctg gtcaaaggct tctatcccag cgacatcgcc    720

gtggagtggg agagcaatgg gcagccggag aacaactaca agaccacgcc tcccgtgctg    780

gactccgacg gctccttctt cctctacagc aagctcaccg tggacaagag caggtggcag    840
```

```
caggggaacg tcttctcatg ctccgtgatg catgaggctc tgcacaacca ctacacgcag    900

aagagcctct ccctgtctcc gggtaaa                                        927


<210> SEQ ID NO 9
<211> LENGTH: 59
<212> TYPE: PRT
<213> ORGANISM: Homo sapien

<400> SEQUENCE: 9

Thr Leu Cys Gly Ala Glu Leu Val Asp Ala Leu Gln Phe Val Cys Gly
 1               5                  10                  15

Asp Arg Gly Phe Tyr Phe Asn Lys Pro Thr Gly Tyr Gly Ser Ser Ser
            20                  25                  30

Arg Ser Arg Gly Ile Val Glu Glu Cys Cys Phe Arg Ser Cys Asp Leu
        35                  40                  45

Ala Leu Leu Glu Thr Tyr Cys Ala Thr Pro Ala
    50                  55


<210> SEQ ID NO 10
<211> LENGTH: 177
<212> TYPE: DNA
<213> ORGANISM: Homo sapien

<400> SEQUENCE: 10

acgctctgcg gggctgagct ggtggatgct cttcagttcg tgtgtggaga caggggcttt     60

tatttcaaca agcccacagg gtatggctcc agcagtcgga gccgtggcat cgttgaggag    120

tgctgtttcc gcagctgtga cctggccctc ctggagacgt actgtgctac ccccgcc       177


<210> SEQ ID NO 11
<211> LENGTH: 334
<212> TYPE: PRT
<213> ORGANISM: Homo sapien

<400> SEQUENCE: 11

Met Gly Lys Ile Ser Ser Leu Pro Thr Gln Leu Phe Lys Cys Cys Phe
 1               5                  10                  15

Cys Asp Phe Leu Lys Val Lys Met His Thr Met Ser Ser Ser His Leu
            20                  25                  30

Phe Tyr Leu Ala Leu Cys Leu Leu Thr Phe Thr Ser Ser Ala Thr Ala
        35                  40                  45

Thr Leu Cys Gly Ala Glu Leu Val Asp Ala Leu Gln Phe Val Cys Gly
    50                  55                  60

Asp Arg Gly Phe Tyr Phe Asn Lys Pro Thr Gly Tyr Gly Ser Ser Ser
65                  70                  75                  80

Arg Ser Arg Gly Ile Val Glu Glu Cys Cys Phe Arg Ser Cys Asp Leu
                85                  90                  95

Ala Leu Leu Glu Thr Tyr Cys Ala Thr Pro Ala Asp Lys Thr His Thr
            100                 105                 110

Cys Pro Pro Cys Pro Ala Pro Glu Leu Leu Gly Gly Pro Ser Val Phe
        115                 120                 125

Leu Phe Pro Pro Lys Pro Lys Asp Thr Leu Met Ile Ser Arg Thr Pro
    130                 135                 140

Glu Val Thr Cys Val Val Val Asp Val Ser His Glu Asp Pro Glu Val
145                 150                 155                 160

Lys Phe Asn Trp Tyr Val Asp Gly Val Glu Val His Asn Ala Lys Thr
                165                 170                 175
```

-continued

```
Lys Pro Arg Glu Glu Gln Tyr Asn Ser Thr Tyr Arg Val Val Ser Val
            180                 185                 190

Leu Thr Val Leu His Gln Asp Trp Leu Asn Gly Lys Glu Tyr Lys Cys
        195                 200                 205

Lys Val Ser Asn Lys Ala Leu Pro Ala Pro Ile Glu Lys Thr Ile Ser
    210                 215                 220

Lys Ala Lys Gly Gln Pro Arg Glu Pro Gln Val Tyr Thr Leu Pro Pro
225                 230                 235                 240

Ser Arg Asp Glu Leu Thr Lys Asn Gln Val Ser Leu Thr Cys Leu Val
                245                 250                 255

Lys Gly Phe Tyr Pro Ser Asp Ile Ala Val Glu Trp Glu Ser Asn Gly
            260                 265                 270

Gln Pro Glu Asn Asn Tyr Lys Thr Thr Pro Pro Val Leu Asp Ser Asp
        275                 280                 285

Gly Ser Phe Phe Leu Tyr Ser Lys Leu Thr Val Asp Lys Ser Arg Trp
    290                 295                 300

Gln Gln Gly Asn Val Phe Ser Cys Ser Val Met His Glu Ala Leu His
305                 310                 315                 320

Asn His Tyr Thr Gln Lys Ser Leu Ser Leu Ser Pro Gly Lys
                325                 330
```

<210> SEQ ID NO 12
<211> LENGTH: 1002
<212> TYPE: DNA
<213> ORGANISM: Homo sapien

<400> SEQUENCE: 12

```
atgggaaaaa tcagcagtct tccaacccaa ttatttaagt gctgcttttg tgatttcttg     60

aaggtgaaga tgcacaccat gtcctcctcg catctcttct acctggcgct gtgcctgctc    120

accttcacca gctctgccac ggctacgctc tgcggggctg agctggtgga tgctcttcag    180

ttcgtgtgtg gagacagggg cttttatttc aacaagccca cagggtatgg ctccagcagt    240

cggagccgtg gcatcgttga ggagtgctgt ttccgcagct gtgacctggc cctcctggag    300

acgtactgtg ctacccccgc cgacaaaact cacacatgcc caccgtgccc agcacctgaa    360

ctcctggggg gaccgtcagt cttcctcttc cccccaaaac ccaaggacac cctcatgatc    420

tcccggaccc ctgaggtcac atgcgtggtg gtggacgtga gccacgaaga ccctgaggtc    480

aagttcaact ggtacgtgga cggcgtggag gtgcataatg ccaagacaaa gccgcgggag    540

gagcagtaca acagcacgta ccgtgtggtc agcgtcctca ccgtcctgca ccaggactgg    600

ctgaatggca aggagtacaa gtgcaaggtc tccaacaaag ccctcccagc ccccatcgag    660

aaaaccatct ccaaagccaa agggcagccc cgagaaccac aggtgtacac cctgccccca    720

tcccgggatg agctgaccaa gaaccaggtc agcctgacct gcctggtcaa aggcttctat    780

cccagcgaca tcgccgtgga gtgggagagc aatgggcagc cggagaacaa ctacaagacc    840

acgcctcccg tgctggactc cgacggctcc ttcttcctct acagcaagct caccgtggac    900

aagagcaggt ggcagcaggg gaacgtcttc tcatgctccg tgatgcatga ggctctgcac    960

aaccactaca cgcagaagag cctctccctg tctccgggta aa                      1002
```